(12) United States Patent
Vickers et al.

(10) Patent No.: US 11,739,546 B2
(45) Date of Patent: Aug. 29, 2023

(54) MODULAR SHELTER PODS

(71) Applicant: Empowerment Innovation Lab, Seattle, WA (US)

(72) Inventors: Nicole Vickers, Seattle, WA (US); Mallory Hall, Seattle, WA (US); Natasha Weiss, Seattle, WA (US); Matthew Koch, Seattle, WA (US)

(73) Assignee: Empowerment Innovation Lab, Seattle, WA (US)

( * ) Notice: Subject to any disclaimer, the term of this patent is extended or adjusted under 35 U.S.C. 154(b) by 377 days.

(21) Appl. No.: 16/985,684

(22) Filed: Aug. 5, 2020

(65) Prior Publication Data
US 2022/0042342 A1 Feb. 10, 2022

(51) Int. Cl.
| | | |
|---|---|---|
| *E04H 1/12* | (2006.01) | |
| *A61L 2/10* | (2006.01) | |
| *E04H 15/00* | (2006.01) | |
| *E04H 15/48* | (2006.01) | |
| *E04H 15/10* | (2006.01) | |

(52) U.S. Cl.
CPC ............. *E04H 1/1205* (2013.01); *A61L 2/10* (2013.01); *E04H 1/1216* (2013.01); *E04H 1/1277* (2013.01); *E04H 15/008* (2013.01); *E04H 15/10* (2013.01); *E04H 15/48* (2013.01)

(58) Field of Classification Search
CPC ... E04H 1/1205; E04H 1/1216; E04H 1/1277; A61L 2/10; A61L 2202/11; A61L 2202/25
USPC ..... 52/79.1, 79.5, 79.9, 220.8, 236.3, 302.7, 52/592.5, 592.6, 742.13
See application file for complete search history.

(56) References Cited

U.S. PATENT DOCUMENTS

| | | | | | |
|---|---|---|---|---|---|
| 3,923,134 | A | * | 12/1975 | Rezazadeh | G07F 9/002 381/167 |
| 5,203,707 | A | * | 4/1993 | Musto | G09B 19/00 434/226 |
| 6,402,338 | B1 | * | 6/2002 | Mitzel | F21S 9/037 362/183 |

(Continued)

FOREIGN PATENT DOCUMENTS

| | | | | |
|---|---|---|---|---|
| EP | 3912649 A1 | * | 11/2021 | ............... A47F 9/04 |
| JP | 06322832 A | * | 11/1994 | |

(Continued)

*Primary Examiner* — Robert Canfield
(74) *Attorney, Agent, or Firm* — Davis Wright Tremaine LLP

(57) ABSTRACT

A modular shelter pod and system are described herein. In one example, a pod may be formed by a number of foldable or detachable panels, where a first panel includes at least four cavities at first locations having a first shape and a first cross section. A second panel may include at least four tabs at second locations corresponding to the first locations, and having a second shape and a second cross section that fits into and engages the at least four first cavities, such that the at least four tabs engage the at least four cavities to resist movement between different pods when arranged vertically. The pod may additionally include a third panel removably connecting the first panel and the second panel and forming an opening defining a cleaning port that is sealable, where the cleaning port is shaped to removably engage a cleaning device.

20 Claims, 8 Drawing Sheets

(56) References Cited

U.S. PATENT DOCUMENTS

| | | | |
|---|---|---|---|
| 6,691,451 B1* | 2/2004 | Keenan | A01K 97/06 |
| | | | 134/186 |
| 6,981,347 B1* | 1/2006 | Walburger | E04H 3/02 |
| | | | 52/36.2 |
| 8,763,315 B2* | 7/2014 | Hartman | E04H 1/005 |
| | | | 52/79.5 |
| 8,769,890 B2* | 7/2014 | Amin | H02G 3/22 |
| | | | 52/220.8 |
| 10,590,671 B1* | 3/2020 | Jee | E04H 9/10 |
| 2006/0147618 A1* | 7/2006 | Kwon | B05B 15/55 |
| | | | 118/302 |
| 2006/0196132 A1* | 9/2006 | Ruano | E04B 1/34823 |
| | | | 52/236.3 |
| 2007/0006369 A1* | 1/2007 | Sagy | E03D 9/037 |
| | | | 4/227.1 |
| 2008/0133255 A1* | 6/2008 | Schau | G06Q 20/127 |
| | | | 705/1.1 |
| 2011/0056147 A1* | 3/2011 | Beaudet | E04B 1/34869 |
| | | | 52/79.9 |
| 2011/0265396 A1* | 11/2011 | Heather | B65D 90/0026 |
| | | | 52/79.9 |
| 2015/0143758 A1* | 5/2015 | McDaniel, Jr. | E04H 15/18 |
| | | | 52/79.5 |
| 2015/0184414 A1* | 7/2015 | Vaidya | E04C 2/02 |
| | | | 428/313.9 |
| 2016/0166721 A1* | 6/2016 | Brown | A61L 2/20 |
| | | | 422/26 |
| 2016/0235876 A1* | 8/2016 | Leyva | A61L 2/202 |
| 2016/0250368 A1* | 9/2016 | Brown | A61L 2/208 |
| | | | 422/110 |
| 2018/0236117 A1* | 8/2018 | Agmont E Silva | B08B 9/08 |
| 2018/0291614 A1* | 10/2018 | Evert | E04H 9/06 |
| 2018/0371733 A1* | 12/2018 | Childress | A61L 2/10 |
| 2019/0054945 A1* | 2/2019 | Bishop | B62B 3/12 |
| 2019/0070325 A1* | 3/2019 | Preminger | A61L 2/10 |
| 2020/0030860 A1* | 1/2020 | Andersen | B01F 27/91 |
| 2020/0179996 A1* | 6/2020 | Cornelissen | B01J 19/24 |
| 2021/0208173 A1* | 7/2021 | Lighton | G01N 35/00623 |
| 2021/0363767 A1* | 11/2021 | Wabst | A61L 2/10 |
| 2022/0040344 A1* | 2/2022 | Okumura | A61L 2/24 |
| 2022/0133925 A1* | 5/2022 | Gray | A61L 2/26 |
| | | | 250/455.11 |

FOREIGN PATENT DOCUMENTS

| | | | | |
|---|---|---|---|---|
| WO | WO-0213910 A1 | * | 2/2002 | E04H 1/1277 |
| WO | WO-2009144761 A2 | * | 12/2009 | A61H 33/066 |
| WO | WO-2016046531 A1 | * | 3/2016 | E04B 1/34321 |
| WO | WO-2021075496 A1 | * | 4/2021 | |

* cited by examiner

MODULAR SHELTER PODS

BACKGROUND

There presently exists a large number of homeless individuals, and other people needing short term shelter. Current homeless shelters and affordable and temporary housing options have not been adequate in addressing this societal issue and have not provided relief to affected individuals. Safety, privacy, sanitation, and cost of these systems and other issues have presented challenges for large scale solutions to work effectively. Accordingly, improvements can be made in the field of temporary housing and shelter systems.

Figure 1:
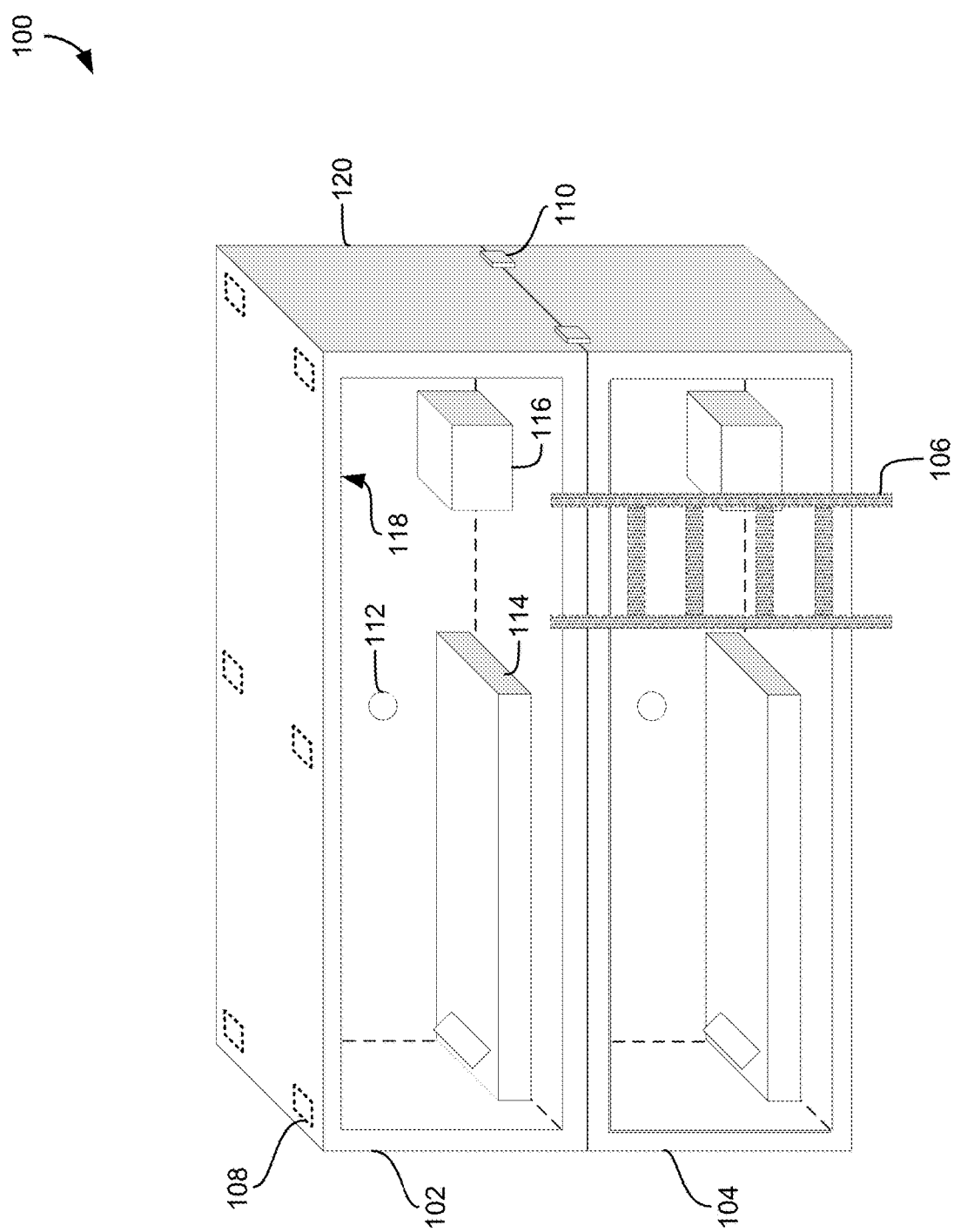
FIG. 1 illustrates an example of two modular shelter pods, according to at least one embodiment.

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Currently, capacity in homeless shelters exists, but is not being fully utilized. In addition, existing infrastructure in these shelters, such as bunk beds, mats, sheer floor space, etc., can actually impede capacity in many cases. Homeless individuals and others needing temporary housing choose sleeping in cars/outside over shelters due to lack of cleanliness, limited privacy, and unsafe shelter conditions. According to multiple organizations, in 2019, the homelessness count in the greater Seattle Area was around 12,500 individuals on any given night. Even with shelters not all being at full capacity, individuals still choose streets, vehicles or abandoned buildings to sleep. Available data would indicate that only about 25% of people referred to shelters decide to say in the shelter. This may be due to a number of reasons.

First, people may not feel safe in shelters. This may be because of a perceived danger: those with mental health problems, such as schizophrenia, fear large groups, especially sleeping out in the open with large groups. Feeling unsafe may also be due to fear of having items taken, as there is typically nowhere to lock or secure personal belongings in existing temporary shelter systems. Privacy may be another detractor from higher shelter usage, which may be due to lack of personal space, higher rate of theft of personal belongings, etc.

Health or hygiene issues are common or at least perceived as common, including bedbugs, body lice, and vermin, and may further discourage higher occupancy in shelters. Hygiene related issues, including close quarter sleeping arrangements and lack of ability to quarantine, may further exacerbate the spread of illness, viruses, etc. The lack of ability to routinely clean and disinfect shelter spaces may further cause hygiene related issues and complications. In addition, violence within shelters is a perceived danger, particularly in the case of more vulnerable individuals, including women, elderly, etc.

Discovery, recognition, and identification of the above noted problems with current sleeping systems for groups of people, including particularly transient, short stay, and homeless individuals, led the Applicant to develop the described modular shelter pod and system, as described in more detail below.

Techniques described and suggested herein include methods and systems for collapsible modular shelter pods, to help provide shelter to people, particularly individuals without the means for other traditional shelter options, while still providing a higher level of safety, privacy, and sanitation. The described shelter pod system includes a number of individual sleeping pods, which may be stackable and securable or lockable together to better utilize limited space for providing shelter for a larger number of people. The pods may be made of any or a variety of composite or plastic materials, such as may provide insulation (e.g., via foam used in part of the panels, air in between plastic surfaces of the panels, etc.) from the surrounding environment, and may be collapsible, such that they can be more readily transported to a site, easily constructed, deconstructed, and moved as needed.

In some cases, the shelter pod may be designed to have an opening on one or more sides to serve as an entry/exit point into the pod. The opening may be large enough to enable viewing of the entire inside space of the pod, thus discouraging unwanted activity in the pod. In some cases, one or more walls of the pod may be perforated or made of fabric, to provide some privacy, but enable light to enter the pod. In one example design, the pod may be large enough to house a single bed (e.g., a twin-sized or other sized bed), and have some storage space for personal belongings. In some cases, the pods may be designed with insert holes or attachment points to attach various additional items inside/outside of the pod, including curtains, a clock, lights (e.g., LED, battery powered lights, or standard plugin-lights), hooks or other means for storing personal items, and so on.

In some cases, one or more panels or members (e.g., walls, a floor, and a ceiling) may be connected together to form a 5 or 6 sided structure. The individual panels may be attached to one or more other panels via bracket or brace, or a hinge mechanism with a locking feature, such that panels may be unfolded and assembled to create the structure, and folded and stacked together for more efficient transportation of the components of the structure. In some cases, one or more panels may completely detach from one another, so that upon disassembly, the panels of the structure may be easily stackable. The shelter pods may be made stackable (when constructed) via one or more interlocking grooves disposed on the ceiling/floor panels of different pods that help align and hold the pods stationary relative to one another. A locking connector (clasp, or other mechanical device) may be further implemented to increase safety and stability of the pods when stacked together.

In some aspects, two or more of the panels may be the same dimensions to enable swapping of the panels in constructing a pod. In some cases, two panels may the same dimensions, with one panel having one or more of a cleaning port, utility port (e.g., for heat, electric, such as a standard plug, USB port, etc.), a drain, a window, or an opening, and the other panel not having that same element or elements, to enable different configurations or arrangements of multiple pods in a space. In some cases, this may include placing a cleaning port on one side for one pod, and on the opposite side for another pod, so they may be placed adjacent to each other and still facilitate cleaning. The same may be done with drains or drain exits (e.g., through a side panel of a pod), openings (e.g., entry point into the pod, such as may accommodate a door, screen, curtain, etc.), openings for windows, or various other features. In some cases, the panels may all be of the same dimensions, with perforations or other removable tabs or the like, to enable customization of a panel for a certain placement in construction of a pod. This may include perforations for a cleaning port, part or all of the drain system, or to separate two pieces of a panel to form side walls.

In some aspects, the floor panel of the pod may have a slight slope leading to a drain and conduit in the floor to enable rapid cleaning and draining of a cleaning agent from the pod, which may occur daily or upon a switch of tenants. In some cases, the pods may be cleaned or sanitized using simple soap and water, with the water draining out of the floor drain. In some aspects, the drain may be placed near a back corner of the pod, so that when stacked a drain pipe (or nothing at all) may be easily installed to connect and/or align the drains of the stacked pods, to provide efficient draining. In some cases, a conduit may connect the drain in the floor member and direct water or other liquid contents out to a side of the pod (e.g., routed through the floor of the pod). A coupler may be used to attached additional conduit or pipe to the side exiting drain conduit, so as to provide a drain mechanism that can be adapted to different installation sites to route the contents to different locations external to and spaced a distance away from the pod.

In some aspects, the pod may include a sealable outlet or port in one of the walls of the pod, which accommodates the insertion of a UVC bulb to readily clean and sanitize each individual pod. In some cases, the UVC bulb may be permanently or semi-permanently installed in each pod. In other cases, a closable opening (e.g., a latch) may be provided in a wall (or in the floor or ceiling) to enable one UVC device to be used to clean multiple pods, by inserting the device into the pod through the latch, cleaning the unit, then removing it and closing the latch. The latch may be opened from the outside or inside of the pod to enable placement of the UVC device into the pod. After application of electricity to the UVC device for a short duration, the pod may be sanitized, and the UVC device removed, whereby the latch may seal the opening in the wall (e.g., via a water tight seal). In some aspects, the latch concept may be used with one or both of the UVC cleaning device or a soap and water cleaning method (manual or at least partially automated), to provide for flexibility in sanitation options.

The collapsible modular shelter pod system, as described herein may provide various advantages over know temporary housing systems, including one or more of increased mobility, decreased cost, adaptable configurations via stacking and construction to accommodate deployment in different spaces (stacking, cleaning systems, etc.), increased housing density while maintaining a high level of sanitation, and/or additional advantages and benefits as may be appreciated and described below.

FIG. 1 illustrates an example pod system 100 including two modular shelter pods 102 and 104, with pod 102 stacked on top of pod 104. As illustrated, each pod 102, 104 may be of a uniform size so as to be stackable and to enable efficient production of exchangeable or modular components of the pods 102, 104. The dimensions of the pod may be selected to house at least a bed 114, such as a twin sized bed, or a larger bed, and any additional items, such as a safe or lockable compartment 116, and/or other items. An opening may be formed in one of the walls of each pod 102, 104, such as opening 118, to enable access to the interior of the pod and to provide visibility into the pod to discourage any unwanted behavior inside the pods (e.g., drug use, etc.). The opening 118 may be any of a variety of shapes and sizes. As illustrated, opening 118 is rectangular and spanning a majority of a long wall of the pod, which forms a rectangular prism. In other cases, the opening may be circular, oval, square, triangular, etc. As illustrated, opening 118 may be located on a longer wall of a pod 102, 104, such as to enable better visibility into the pod, and provide for various configurations of multiple pods to best utilize different spaces, such as multiple pods arranged in a circle or about a central point with the openings facing inward. In other cases, opening 118 may be disposed on a shorter side of the pod, such as side 120, to enable different configurations that can be used in different spaces, in different arrangements, etc. In some cases, a curtain or foldable or hinged wall or door may be provided to cover the opening 118, such as to provide privacy. In some aspects, this closure may be made of a transparent or translucent material to deter unwanted or illegal behavior inside of the pod.

In some aspects, the pods may be configured to support a certain number of pods stacked on top of other pods, where the configuration may include type of material used to form the panels, thickness of material, dimensions of the pod, and the like. In some cases, these different attributes of the pods may be selected to optimize or balance weight of the pods with strength to support a given number of pods stacked on top of one another.

In some cases, pod system 100 may include a removable ladder or other step or access device 106 that may enable access to an upper pod 102, which may be stacked on top of a lower pod 104. The ladder 106 may be removable and separate from the pod. In other cases, the ladder 106 may be removably attached to a pod, such as via any number of different mechanisms, including a hook over a lip forming the opening 118, a hinge, bracket, etc. In yet some cases, the ladder may be integrated into a pod, such as a foldable or compressible ladder system that may be stored in a compartment located in or formed by a pod or a panel of a pod. In some cases, ladder devices 106 may be of different sizes to enable access to pods stacked more than 2 pods high, such as 3, 4, 5, or more pods stacked on top of one another. In some cases, these taller ladders may have additional safety features, such as hand rails, or other devices, to enable safer access to pods that are arranged higher off of the ground. In some aspects, ladder device 106 may be connectable, such that each alone is tall enough to span one story, where when the ladders are connected, they can span multiple stories. In some cases step deice 106 may include number of removable platforms that may form steps when inserted into cavities formed in at least one panel of the pod. In some aspects, these steps may be storable in the pod itself, and/or may securely attach to a panel, such as near the opening 118, via a secure mechanism, such as hook or other attachment device.

Each pod 102, 104 may be made stackable by indentations or groves 108 disposed on a top facing member or bottom facing member of the pod, with a protruding member on the opposite face of another pod in alignment with the indentations or grooves 108. In some cases, latches or other mechanical devices 110 may be disposed in or on one or more sides of a pod to enable a secure and removable attachment mechanism to securely attach one pod 102 to another 104. In some cases, there may be one, two, or more latches disposed on one, two, three, or four sides of a pod to enable a secure attachment to another pod. In some aspects, each pod may include the one or more latches near the top or bottom of one or more walls of the pod. In yet some case, the latches may alternate, such that one pod has one or more latches on at least one side of the pod disposed at or near the bottom of the pod, and one or more latches on at least one side of the pod disposed at or near the top of the pod.

In some cases, each pod may have an access port 112, which may be used for cleaning the pod. In some cases, the port 112 may be of a shape and size to accommodate a UVC cleaning device, a water supply, such as a hose or other tube, or may be designed to accommodate both. In some cases, port 112 may be disposed on a wall of a pod and may be sealable, such that when not in use, the port may protect the inside of the pod form the external environment. In other cases, the port 112 may be simply a hole or opening formed in a wall, to enable cleaning of the pod, such as in the case when the pod is designed and used for interior spaces, as opposed to outdoor spaces where a sealable port 112 may be more beneficial.

Figure 2:
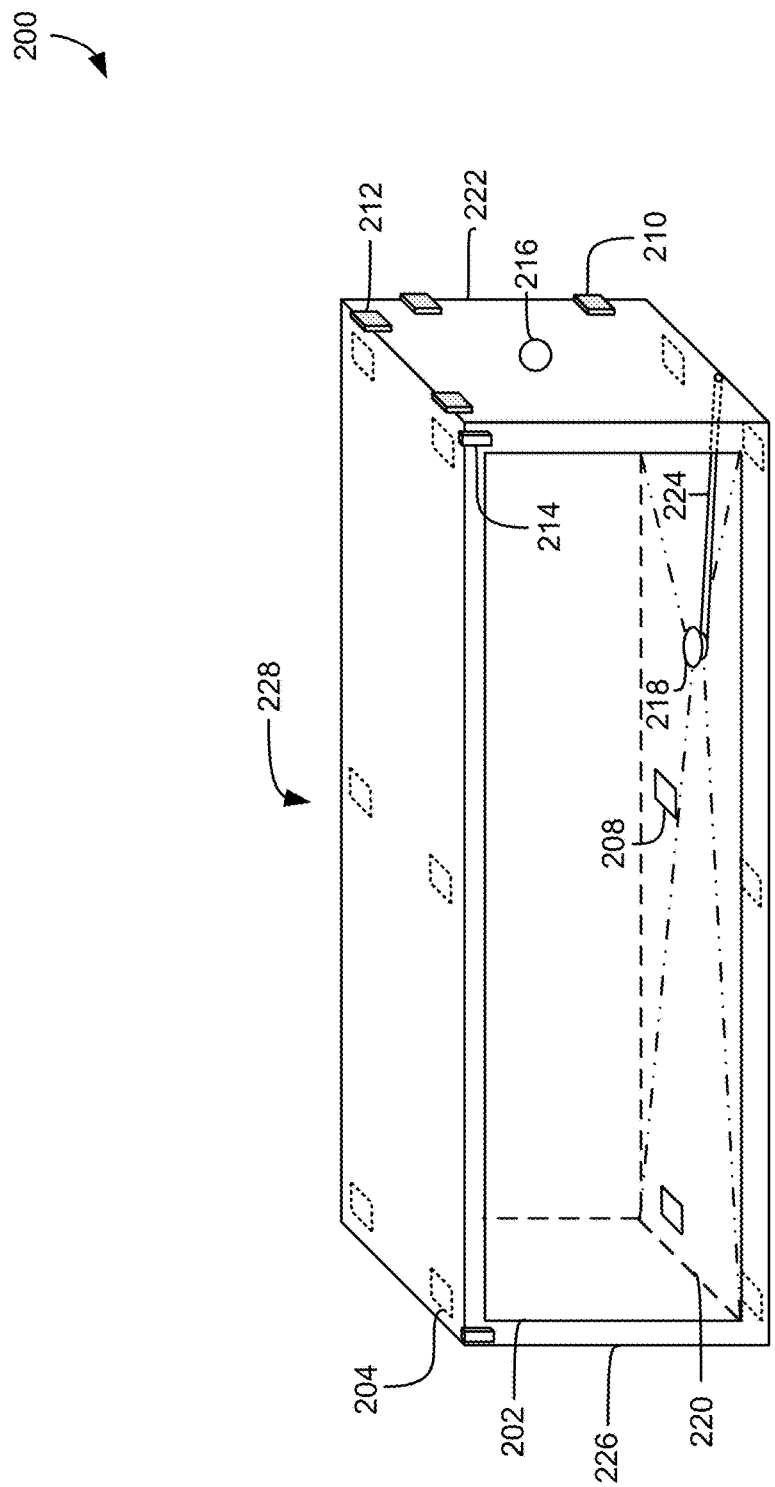
FIG. 2 illustrates another example of a modular shelter pod, according to at least one embodiment.
Figure 3A:
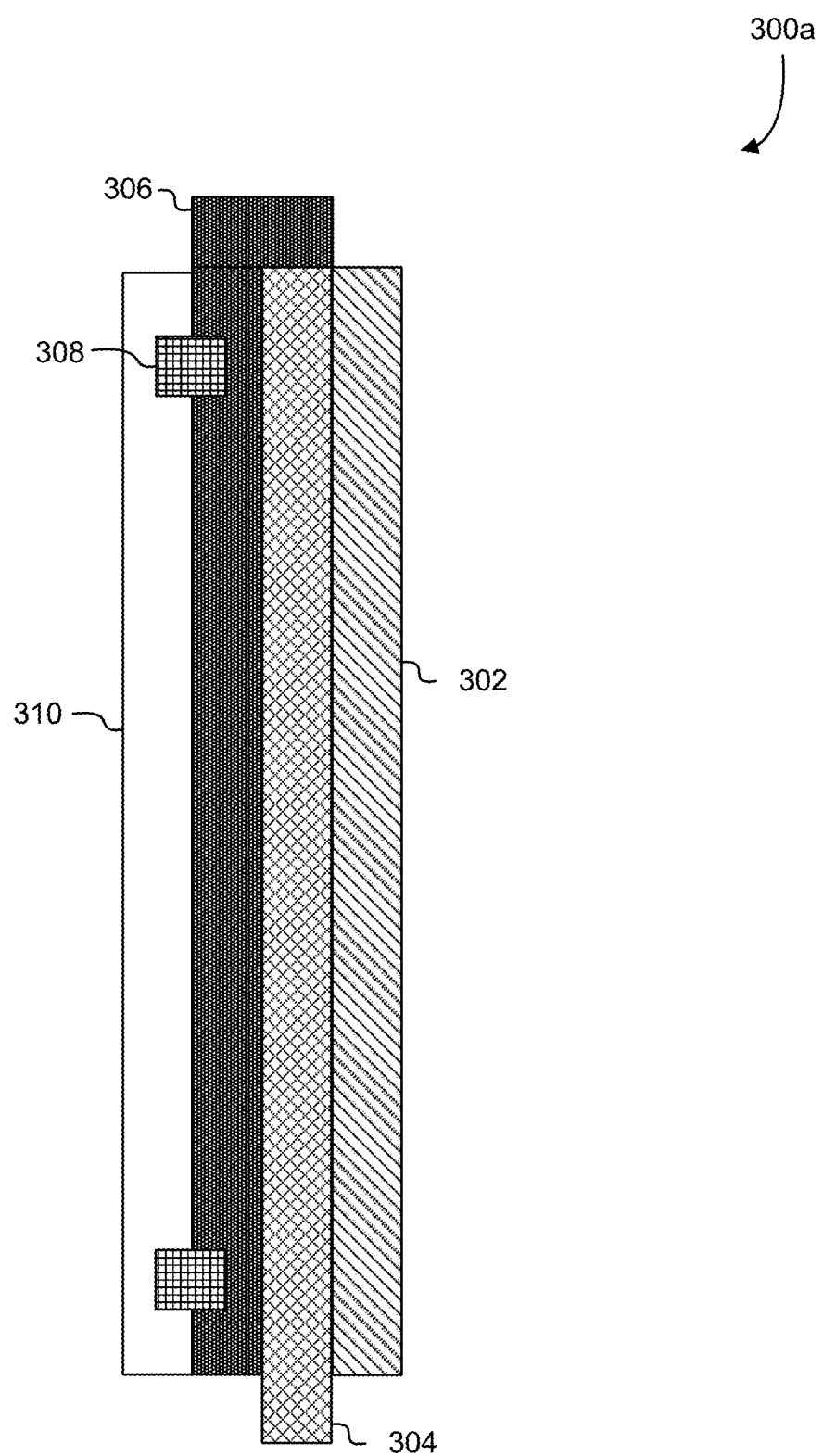
FIGS. 3A-3D illustrate example assembly stages of a modular shelter pod, according to at least one embodiment.
Figure 3B:
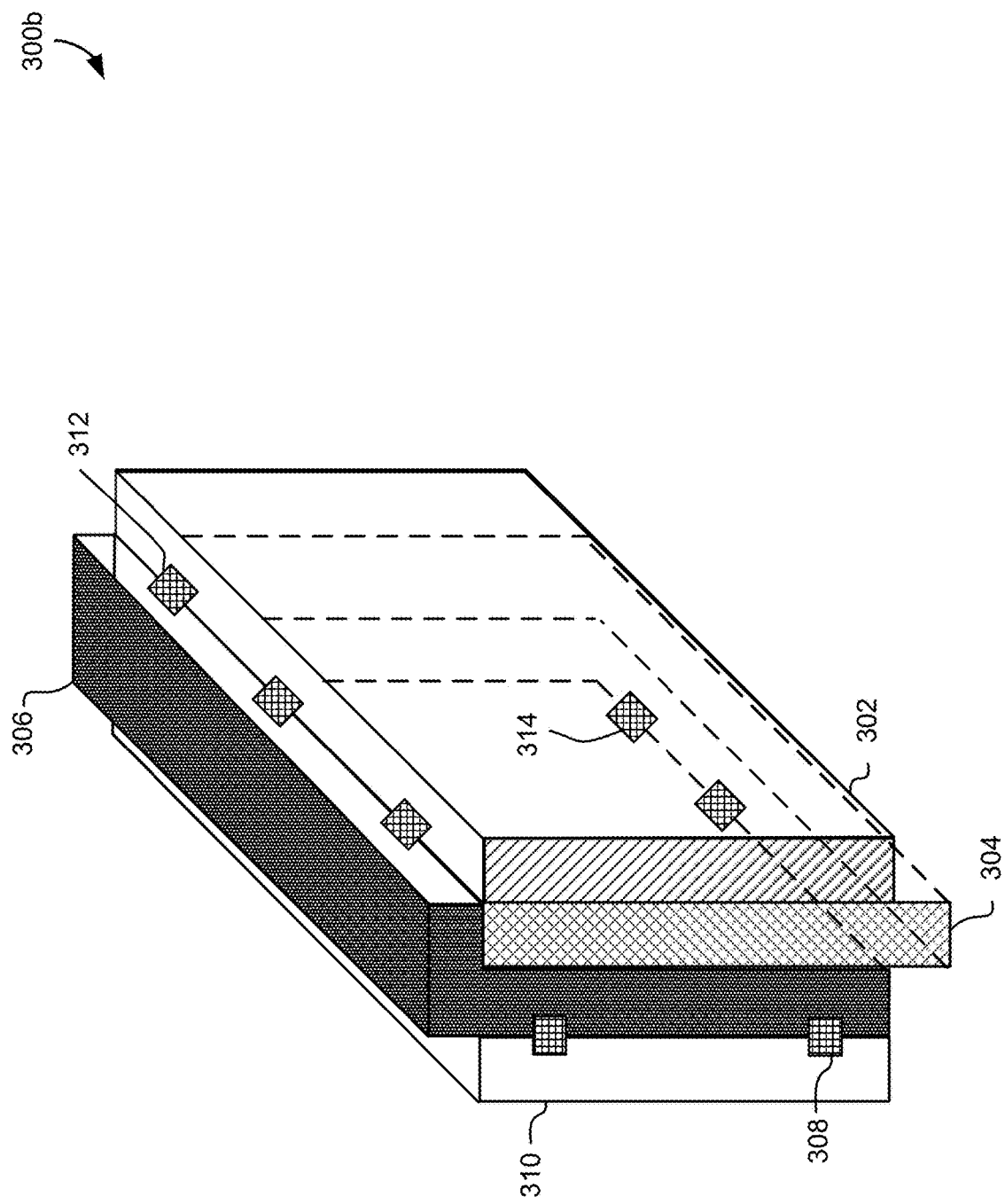
Figure 3C:
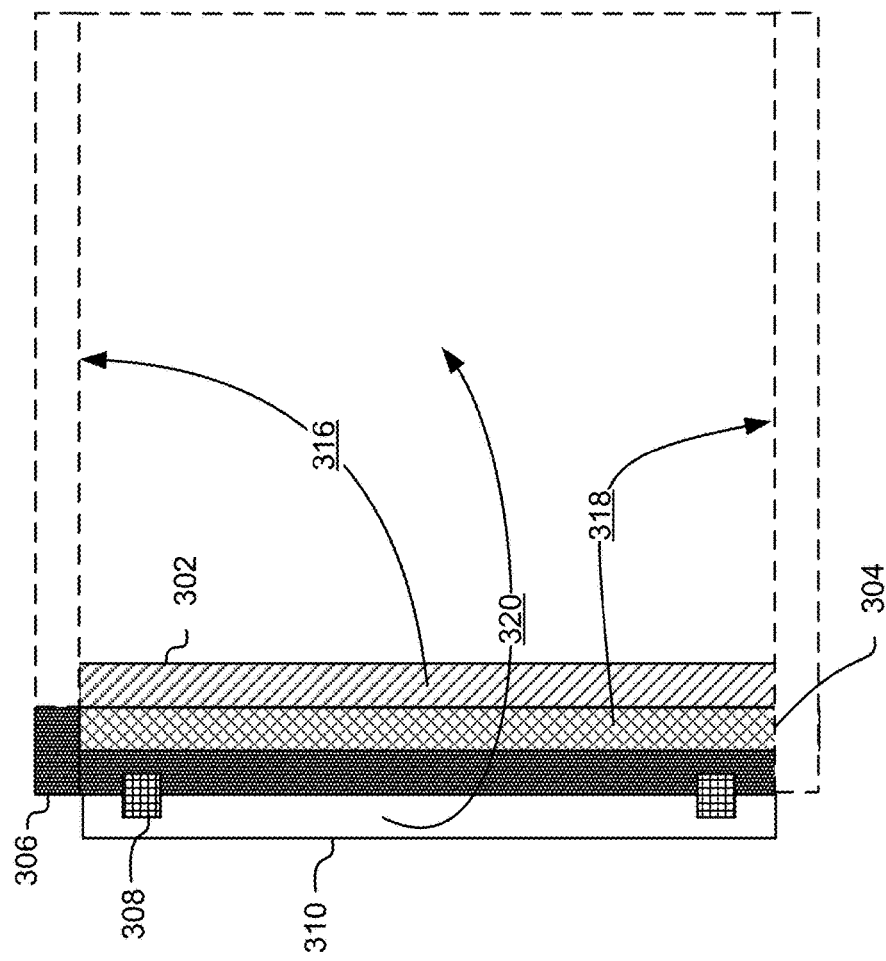
Figure 3D:
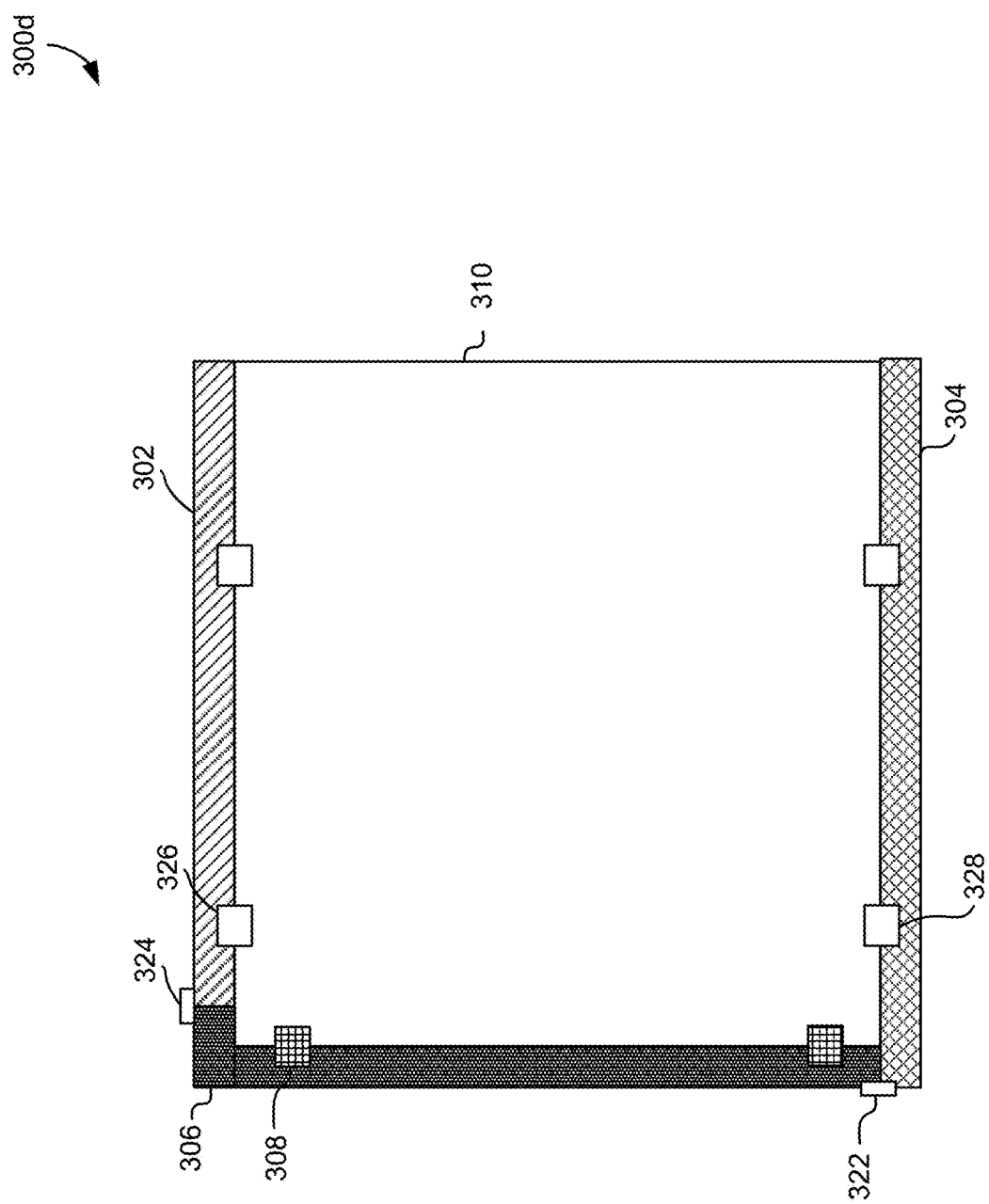

FIG. 2 illustrates another example of a modular shelter pod 200, according to at least one embodiment. It should be appreciated that various features of pod 200 may be combined with pods 102, 104 described above in reference to FIG. 1. As illustrated, pod 200 may include a drain 218, such that may be disposed on a floor or bottom surface 220 of the pod 200. The drain 218 may be formed a least in part in the floor panel or member 220 of the pod. In some cases, the interior surface of floor 220 may slightly pitched downward toward the drain 218 to facilitate draining of any liquid from the pod 200, such as water and/or soap or other cleaning solvent from cleaning the pod. In some cases, drain 218 may located in the center of the floor 220 of the pod. In other cases, the drain 218 may located at some other position on the floor of the pod 200, such as near an exit wall or side 222 of the pod 200. The drain 218 may direct fluids downwards, via one or more conduits 224, to a space below or to a side of the pod 200. The conduit 224 may be formed in the floor 220 of the pod, and in some cases may exit to the side of the pod (e.g., through a side wall of the floor itself of through a wall of the pod), such as to enable pods to be stacked on top of one another and still drain external to the pods. The conduit 224 may be formed of plastic, metal, ABS, or other suitable material that may ensure that water does not leak into an interior of the floor or wall of the pod 200. In some cases, the end of the conduit 224 and/or an exit wall 222 of the pod may be formed to enable attachment of a drain pipe to the pod, to enable directed draining of the pod, such as into a container or to a space a certain distance away from the pod, to, for example, prevent the water from eroding the ground near or underneath the pod, etc.

In some cases, the conduit 224 may direct fluid entering drain 218 directly or substantially downward, such that the conduit terminates on an external surface of the floor 220. In this example an external drain pipe may be attached to the external surface of the pod 200 where the conduit terminates to enable configurable or adjustable direction of liquids being drained from the pod 200. In one example, the external surface of the floor 220 may have one or more open channels formed in the floor to enable external placement of a conduit from the exit of the drain 218 to a side wall of the pod to enable directing liquid drained from the pod away from the pod (e.g., when placed on flat ground, or on another pod). In some cases a channel may be formed on an external surface of the ceiling panel of another pod, such that when pod 200 is stacked on top of the other pod, the fluid may drain to a side of the pod 200 via the channel formed in the other pod.

In yet some cases, one or more pumps may be utilized to direct liquids drained from the pod 200 to other locations, storage tanks, etc., that are located at a position above the drain 218. It should be appreciated that the above implementations of a drain 218 and conduit 224 are only given by way of example, and that various other configurations are contemplated herein.

As illustrated in FIG. 2, in some cases, the cleaning port 216 may located on a short wall 222 of pod 200, such as to facilitate different arrangements of multiple pods stacked or attached to one another. For example, 4 pods 200 may be arranged in a 4-square pattern on the ground or bottom surface, and any number of pods stacked on top, forming levels each having four pods. In this example, some pods may have cleaning ports and/or drain exits on side 222, and other pods may have cleaning ports 216 and drain exits on side 226. In another example, pods may be arranged in rows, such that any number of pods are placed adjacent to each other, with side walls 222, 226 connected, with cleaning ports 216 and drain exits located on back wall 228. Similarly in this arrangement pods may then be stacked on top of each other in various ways. In other cases, where opening 202 is formed on one of short walls 222, 226 various arrangements to similar effect may also be realized.

In some examples, a singular pod may be adaptable to fit in two or more of these various arrangements. This may be realized through the use of cleaning ports that are included on 3 or 4 walls of a pod. In some cases, each cleaning port may have a sealable mechanism that allows the port to be opened or closed, and thus may provide the most versatility in arranging multiple pods in different configurations. In a similar way, conduits may be disposed in the floor and/or walls of a pod that direct liquids from a drain to 2, 3, or 4 sides of the pod. In some cases, this may be realized through a drain rotatably connected to the floor, such that upon rotation, a 90 degree conduit connected to the drain may be aligned with one of multiple exit conduits. In other cases, valves may be attached to each conduit to enable selection of just one conduit. It should be appreciated that other mechanisms may be similarly utilized. In yet some cases, cleaning holes may be pre-formed into multiple walls of a pod, such as via perforations in the shape of the port formed in the wall, whereby once the perforated section is removed, a closing mechanism may be attached. This may decrease cost for each pod, in that only one closing mechanism may be needed per pod, while still enabling different configurations. In yet some cases, one side wall and one longer wall may include perforations, or alternatively, a cleaning port and mechanism, such that upon construction of a pod, the correct wall with a port may be selected for a particular arrangement.

In some cases, a pod may be constructed such that the opening is formed by a lack of an entire wall. In this cases, different configurations may be realized by placing a side wall having a cleaning port on either side of the opening. In some cases, a partial wall forming the opening may be attached in the construction process and may further aid in increasing the structural integrity of the pod.

In some aspects, various latch or connection mechanisms 210, 212, 214 may be included and/or attachable to various walls of a pod to facilitate joining multiple pods together in different configurations securely. In some cases, some or all of the walls of pod 200 may include holes or other attachment means to accept a universal attachment mechanism, such as mechanisms 210, 212, 214, that may be used to attach two pods together, such that the two pods have one adjacent or adjoining wall. The universal attachment mechanism may include a bracket or strap, such as made out of a steel or other metal, wood, plastic or other material. In some cases, the attachment means may be holes (e.g., with threads) or holes having reinforced inserts (e.g., metal insert with threads). In other examples, the attachment mechanism may be a bracket with one more hooks, where the attachment means includes a hole with a bar or other shape to accept and securely hold and the hooks of the attachment mechanism. In yet some examples, the attachment mechanism may include one or more hinges, latches, cables, or other known attachment devices. It should be appreciated that various other attachment mechanisms and attachment means are contemplated herein, and that the above are given by way of example only.

In some cases, the attachment means may not stick out beyond the external surface of the wall on which it is disposed, to enable more efficient stacking of the panels to enable more compact stacking and transport of the walls. In a similar manner, in some cases, the attachment mechanisms may be easily removed from the walls for a similar benefit.

As also illustrated in FIG. 2, pod 200 may include holes or protrusions 204 on one of the top or bottom surface or panel of the pod, with the corresponding opposite hole or protrusion 208 disposed in a corresponding location on the other of the top or bottom surface. These protrusions and holes 204, 208 may take any of a variety of shapes and sizes, and may enable the pods to be securely stacked on top of one another, such as in combination with one or more attachment means 212, 214. Examples of configurations of these holes and protrusions 204, 208 will be described in greater detail below in reference to FIGS. 4A and 4B.

FIGS. 3A-3D illustrate example assembly stages 300a, 300b, 300c, and 300d of a modular shelter pod, according to at least one embodiment. In some aspects, a modular shelter pod may be folded up, such as for transport, to be moved between locations, such as to provide temporary shelter at different locations. In one example, the modular shelter pod may be folded up into a substantial rectangular or planar assembly 300a, to facilitate more efficient transport of the pod, such as made easily stackable so that multiple pods may be transported by single vehicle. In other cases, the shelter pod may be disassembled into a number of separate pieces or components and similarly stacked, to better facilitate efficient transportation.

As illustrated in diagram 300a, a number of panels 302, 304, 306, 310 may be folded onto each other to form a substantially rectangular cross section. In one example, panel 302 may form the ceiling, panel 304 may form the floor, panel 306 may form a back wall (e.g., opposite the opening) and panel 310 may include two half-length panels that each form the sides of the pod. Each panel may be connected to at least one other panel via a hinge or hinge type mechanism. In one example, ceiling panel 302 may be rotatably connected to back wall 306, with part of the back wall also forming part of the ceiling. Floor panel 304 may be rotatably connected to the back wall 306. Each of panels 310 may be rotatably connected also to back wall 310 via a hinge mechanism, such as mechanism 308. It should be appreciated that multiple hinge mechanisms (1, 2, 3, or more) and or different hinge mechanisms may be used for connecting different panels together.

In some cases, mechanism 308 may include metal or plastic hinges fastened to the panels. In yet other cases, mechanism 308 may include folding plastic, composite, or metal seams between two panels. In yet other examples, mechanism 308 may include a hole and pin structure, whereby one edge of one panel has holes or indentions formed in it, and a corresponding edge of another panel has pegs or protrusions that align with and fit into the holes of the other panel. In yet other cases, mechanism 308 may include two corresponding hinge pieces that are at least partially formed as part of two panels, such that when two panels are placed together and their hinge pieces aligned, a pin (e.g., plastic or metal) may be inserted between both hinges to connect the two panels together.

Diagram 300b illustrates a perspective view of the same panels in a folded arrangement, with multiple hinges 308, 314, and 312 connecting the various panels.

Diagram 300c illustrates a first stage of assembling the pod from the folded arrangements 300a, 300b. As illustrated, the ceiling panel 302 may be first rotated and moved upward at operation 316. Next, the floor panel 304 may be rotated and moved downward at operation 318. Next, the side panels 310 may be rotated and moved around the back wall 306, to form an assembled pod 300d. As illustrated in diagram 300d, one or more latches or other securing devices 326 and 328 (and corresponding devices on the other side of the pod) may be attached to secure the side panel 310 to the ceiling and floor panels 302, 304, respectively. Similarly, one or more securing devices 322 and 324 may be used to securely fix in place the floor panel 304 to the back wall panel 306, and the ceiling panel 302 to the back wall panel 306, respectively. It should be appreciated that stages 300a, 300b, 300c, and 300d are only given by way of example, such that various other arrangements, different placements of hinges, different attachments between panels, etc., are contemplated herein.

Figure 4A:
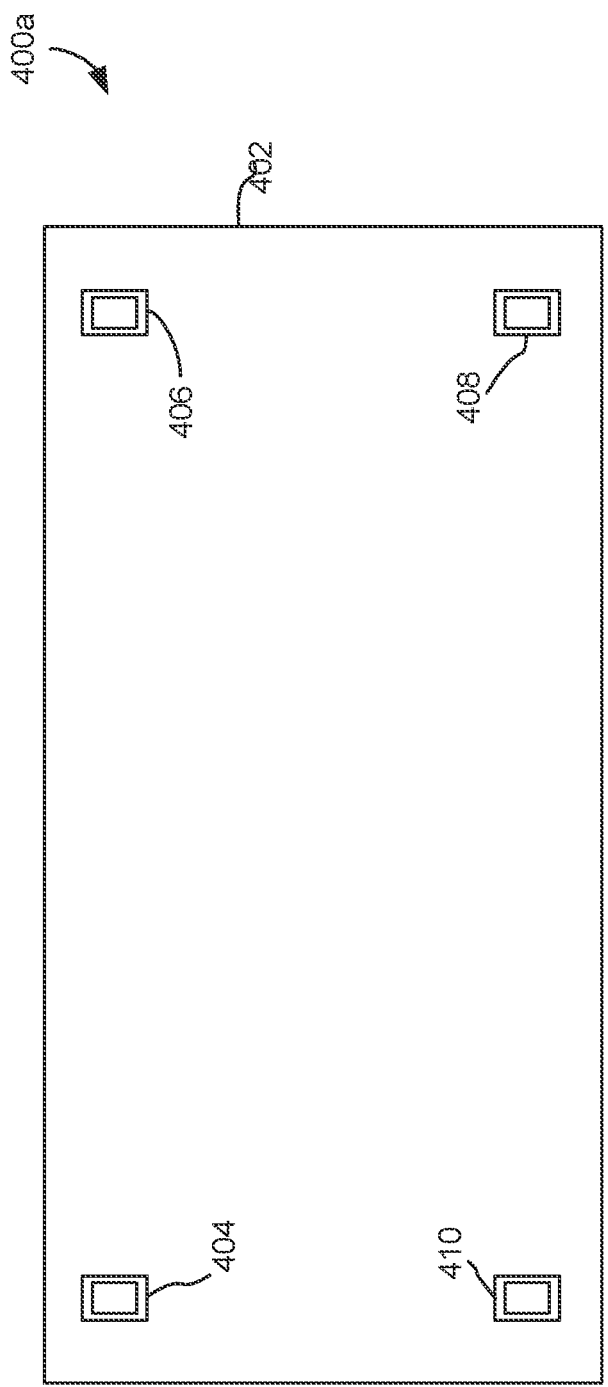
FIGS. 4A-4C illustrate example diagrams of mechanisms used to stack modular shelter pods, according to at least one embodiment.
Figure 4C:
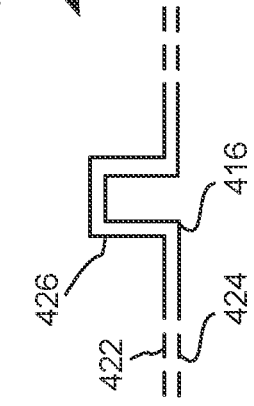
Figure 4B:
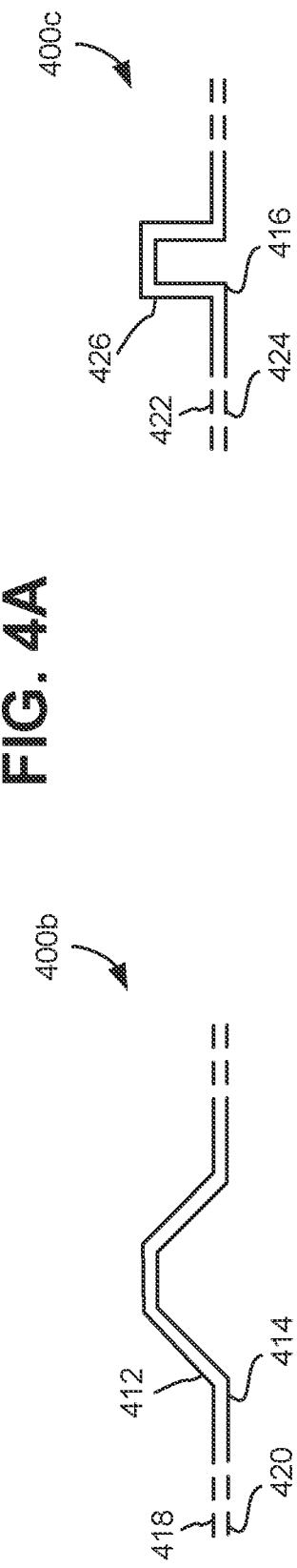

FIGS. 4A-4C illustrate example diagrams 400a, 400b and 400c of mechanisms used to stack modular shelter pods, according to at least one embodiment. Diagram 400a illustrates an example placement of a number of holes/indentations and corresponding protrusions/tabs 404, 406, 408, and 410 on a surface 402, which may be an outer surface of a floor or ceiling panel of a modular shelter pod, such as those described above. The ceiling of one pod may have holes, whereas the floor of another pod may have tabs, or vice versa, such that when the two come in contact, e.g., are stacked, the tabs line up with holes and resist side to side movement between the two pods. As illustrated, 4 holes/tabs are each located proximate to a corner of surface 402. This is only one example arrangement and placement of holes/tabs 404, 406, 408 410. It should be appreciated that other numbers and/or different arrangements of holes/tabs 404, 406, 408 410 may be similarly implemented. In some examples, different shapes (e.g., other than square or rectangular) holes/tabs may be used, including multiple holes/tabs shaped similar to ridges, rings, or various other shapes, or various combinations thereof.

Diagrams 400b and 400c illustrates two cross sections of holes/tabs 412, 414 and 416, 426. In the first example, hole 412 and tab 414 may have a corresponding slanted edge, flat top portion, and another slanted edge, such that the tab fits into the hole whereby the corresponding surfaces 418, 420 of the hole and the tab come into contact. In the second example, hole 426 and tab 416 may have a corresponding square edge (e.g. perpendicular to surfaces 422, 424) flat top portion, and another square edge, such that the tab fits into the hole whereby the corresponding surfaces 422, 424 of the hole and the tab come into contact. It should be appreciated that other cross section profiles of holes and tabs may be similarly implemented, for example, based on the size of the pod, number of holes/tabs, weight of the pods, type of surface of the floor and/or ceiling panels used, the friction provided between those surfaces, and so on. In a similar way, the number of holes and tabs, shapes of the holes and tabs, position, arrangement etc., may be selected for a specific design of pods based on the same or different factors.

Figure 5:
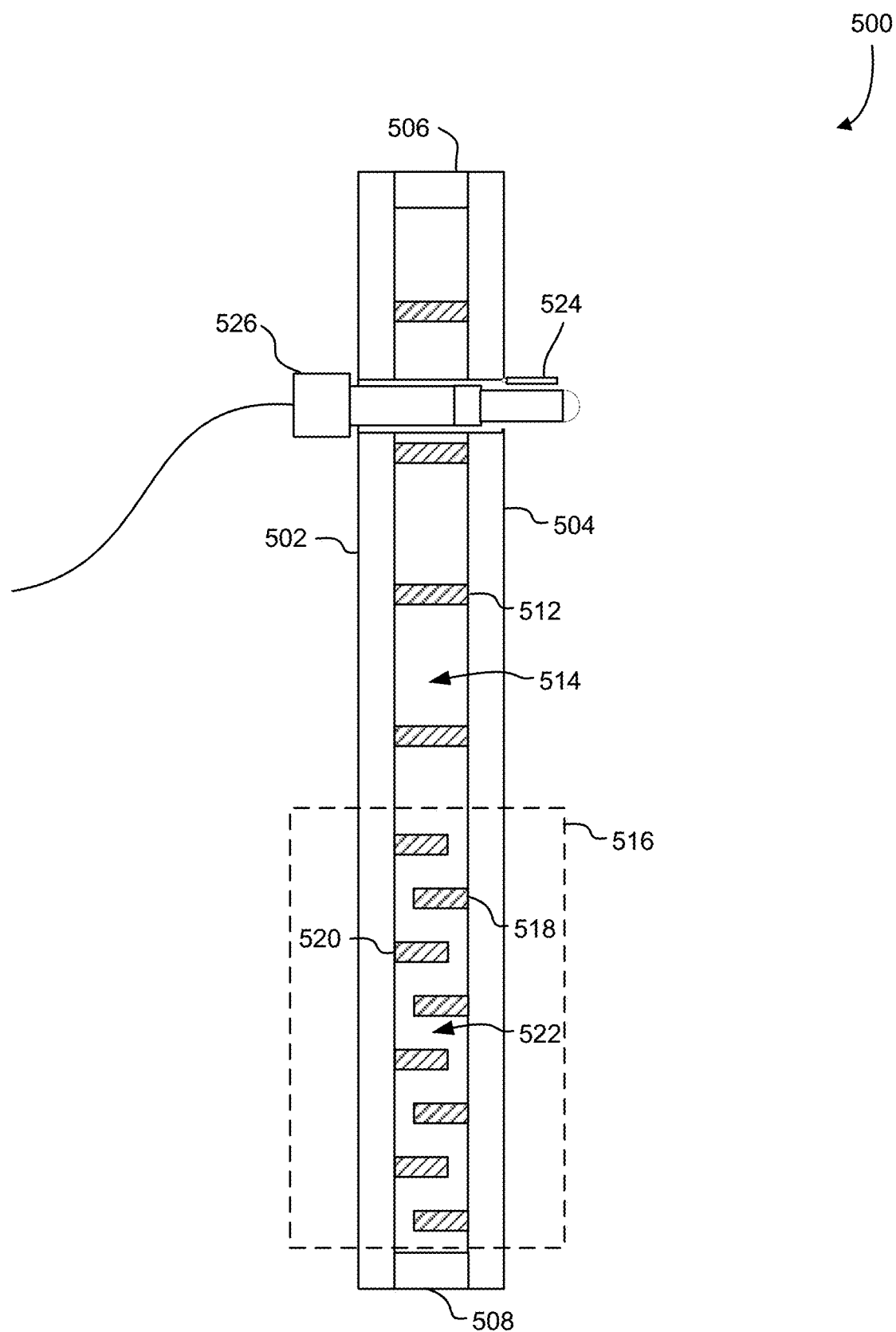
FIG. 5 illustrates an example cross sectional view of a panel of modular shelter pod, according to at least one embodiment.

FIG. 5 illustrates an example cross sectional view of a panel 500 of a modular shelter pod, according to at least one embodiment. In the example illustrated panel 500 may be a wall panel, such as may include a cleaning port 524. However, it should be appreciated that construction of a ceiling or floor panel may share one or more aspects as panel 500.

In some aspects panel 500 may include outer sheets 502 and 504, which may be made of a composite material, such as any of a variety of plastics, with a thickness selected to support the weight of another pod or multiple pods. In some aspects, sheets 502 and 504 may be made of the same or different materials and/or have the same or different characteristics. For example, sheet 502 may be an outward facing sheet, such that it may be exposed to outside elements. In some aspects, sheet 502 may be constructed of any of a variety of plastics or composite material, such as PVC, polycarbonate, fiber reinforced polymer (FRP), fiberglass, wood or wood products or sheets, various metals, and so on, or a combination thereof. In this example, sheet 504 may be an inward facing sheet, such that it may be arranged to face the interior of the pod. In this case, sheet 504 may be made of any of the same materials as sheet 502. In some aspects, sheet 504 material may be selected to provide a comfortable environment for sleeping, etc., and may not be as resilient to environment concerning (e.g., may not be water proof, etc.). In some cases, the materials and/or thickness used for sheets 502 and 504 may be selected to be strong enough to safely support one or a more pods to be stacked on top of each other, and the materials and thickness may be different (e.g., a thin veneer material used for sheet 504, whereas stronger structural material could be used for sheet 502). In some aspects, one or both of sheets 504 may be coated with one or more materials, such as to enhance sanitation (e.g., sealing coating for wood in interior or exterior applications), and/or protect against environmental conditions (e.g., waterproofing, UV radiation-resistant coatings and the like).

The sheets 502 and 504 may be connected via cap portions 506 and 508, such as may be made out of the same or different composite material as sheets 502, 504. In some examples, caps may be formed together with a sheet 502, 504 to form a single component. In some examples multiple cross supports 512 may be disposed between sheets 502 and 504 to provide structural support and rigidity to panel 500, whereby the space 514 between the cross supports may be filled with ambient air, other gas, or an insulating material. In some cases, the insulating material may be loose fill or blow in insulation, such as fiberglass, mineral wool, or cellulose, or may be a foam board type insulation, such as Polystyrene, Polyurethane, Polyisocyanurate, etc., or other types of insulation, or a combination thereof. In this example, the number and spacing of the cross supports 512 may be selected based on the material used to form the cross supports and/or the sheets 502, 504, the space between the sheets 502, 504, and a desired weight capacity of the panel (which may vary based on whether the panel is to be used as a wall or a floor or ceiling panel in a pod). In an alternative embodiment, illustrated in view 516, cross members 520 may not actually span the entire space between sheets 502, 504, such as to form a continuous channel 522 between the supports 520, where the channel may be filled with air, other gas, or an insulating material.

In some examples, the panels may be produced in a number of different ways. For example, separate exterior faces 502, 504 may be supported with interior framing, such that the framing may be attached to both faces of panels. The interior voids left in the framing may then be infilled with insulation or left empty. In another example, the panels may be formed starting with an interior insulating layer (e.g., rigid foam), with exterior faces 502, 504 attached thereto, such as via glue, lamination, or other means to form a composite or SIP. In yet other examples, the exterior faces 502, 504 may be constructed and integrated with the interior framing.

In some aspects, panel 500 may be formed of a singular or combination of materials material (e.g., a structurally insulated panel (SIP)) to form a singular panel, such as composite, foam, and/or coated with one or various materials to provide enhanced durability environmental exposure (e.g., water resistance, UV protection, etc.), or may be formed of more than one material, such as is known in the art.

In yet some aspects, one or more panels of a pod may be made transparent, translucent, or with portions (e.g., simulated windows) that are transparent or translucent, to provide for enhanced safety and increased visibility into a pod constructed with panel 500. In some cases, one or more of faces or sheets 502 and 504 of panel 500 may be constructed to be flat, i.e., defining a planar surface, or may have ribs or form other profiles, such as for added strength, aesthetics, or for other reasons.

In some aspects, panel 500 may include a cleaning port 524, which may have include an opening in one or both of sheets 502, 504. In some cases, the width and shape of the port 524 may be designed to accommodate a UVC cleaning device 526 or other cleaning device (e.g., garden hose, other water hose, power washer, etc.). In one example, port 524 may include a sealable opening in outer sheet 502 and a sealable opening in inner sheet 504, (illustrated as a latch or sealable mechanism). In some aspects, one or both of the openings may form a water tight seal with sheet 502 and 504, respectively.

In some cases, part or all of panel 500 may be made to be flame retardant or have a flame retardant coating to provide enhanced safety in case of fire. In yet some instances, the interior components of the pod, such as a bed or platform for sleeping, bedding, lockable storage, and other interior components of the pod may also be made flame retardant for similar safety benefits. In some cases, this may include forming the bed platform and other elements out of flame resistant materials, including certain composites, metal, etc.

In some aspects, the construction of panel 500 may be selected to provide a certain level of sound insulation, to provide enhanced privacy and comfort in the interior of the pod.

In yet some aspects, panel 500 may define or have one or more removable openings and/or conduits, such that will accommodate installation of a heating duct and/or an electric cable or line to supply electricity (e.g., power outlet, USB port, etc.), internet, or other conveniences. In some cases, these opening or conduits may be formed into the panel during construction, but only utilized but removing perforated sections of one or more of sheets 502, 504, to enable adaptability and flexibility when using a specific panel for various placements for a given pod. In yet some examples electric lines, outlets, USB ports, and/or heating ducts may be pre-formed or placed into panel 500 to enable faster construction and placement of a pod.

In examples where panels are not connected to other panels via a hinge mechanism (such as in the example described above in reference to FIGS. 3A-3D), but are rather completely detachable, the panels may be coupled together to form a pod via different means. In some examples, the edges of the panels may be ribbed (e.g., interlocking) or flat. In some cases, panels may be connected to each other via fasteners and/or plates or brackets. In yet other examples, panels may be connected via hasps on one or more faces of one or more panels to be attached. In some examples, a combination of folding and detachable panels may be used, to provide flexibility in transportation and efficient assembly of pods at various sites.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. Similarly, use of the term "or" is to be construed to mean "and/or" unless contradicted explicitly or by context. The terms "comprising," "having," "including," and "containing" are to be construed as open-ended terms (i.e., meaning "including, but not limited to,") unless otherwise noted. The term "connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal. The use of the phrase "based on," unless otherwise explicitly stated or clear from context, means "based at least in part on" and is not limited to "based solely on."

Conjunctive language, such as phrases of the form "at least one of A, B, and C," or "at least one of A, B and C," (i.e., the same phrase with or without the Oxford comma) unless specifically stated otherwise or otherwise clearly contradicted by context, is otherwise understood within the context as used in general to present that an item, term, etc., may be either A or B or C, any nonempty subset of the set of A and B and C, or any set not contradicted by context or otherwise excluded that contains at least one A, at least one B, or at least one C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}, and, if not contradicted explicitly or by context, any set having {A}, {B}, and/or {C} as a subset (e.g., sets with multiple "A"). Thus, such conjunctive language is not generally intended to imply that certain embodiments require at least one of A, at least one of B and at least one of C each to be present. Similarly, phrases such as "at least one of A, B, or C" and "at least one of A, B or C" refer to the same as "at least one of A, B, and C" and "at least one of A, B and C" refer to any of the following sets: {A}, {B}, {C}, {A, B}, {A, C}, {B, C}, {A, B, C}, unless differing meaning is explicitly stated or clear from context. In addition, unless otherwise noted or contradicted by context, the term "plurality" indicates a state of being plural (e.g., "a plurality of items" indicates multiple items). The number of items in a plurality is at least two but can be more when so indicated either explicitly or by context.

Operations of processes described herein can be performed in any suitable order unless otherwise indicated herein or otherwise clearly contradicted by context. In an embodiment, a process such as those processes described herein (or variations and/or combinations thereof) is performed under the control of one or more computer systems configured with executable instructions and is implemented as code (e.g., executable instructions, one or more computer programs or one or more applications) executing collectively on one or more processors, by hardware or combinations thereof. In an embodiment, the code is stored on a computer-readable storage medium, for example, in the form of a computer program comprising a plurality of instructions executable by one or more processors. In an embodiment, a computer-readable storage medium is a non-transitory computer-readable storage medium that excludes transitory signals (e.g., a propagating transient electric or electromagnetic transmission) but includes non-transitory data storage circuitry (e.g., buffers, cache, and queues) within transceivers of transitory signals. In an embodiment, code (e.g., executable code or source code) is stored on a set of one or more non-transitory computer-readable storage media having stored thereon executable instructions that, when executed (i.e., as a result of being executed) by one or more processors of a computer system, cause the computer system to perform operations described herein. The set of non-transitory computer-readable storage media, in an embodiment, comprises multiple non-transitory computer-readable storage media, and one or more of individual non-transitory storage media of the multiple non-transitory computer-readable storage media lack all of the code while the multiple non-transitory computer-readable storage media collectively store all of the code. In an embodiment, the executable instructions are executed such that different instructions are executed by different processors—for example, in an embodiment, a non-transitory computer-readable storage medium stores instructions and a main CPU executes some of the instructions while a graphics processor unit executes other instructions. In another embodiment, different components of a computer system have separate processors and different processors execute different subsets of the instructions.

Accordingly, in an embodiment, computer systems are configured to implement one or more services that singly or collectively perform operations of processes described herein, and such computer systems are configured with applicable hardware and/or software that enable the performance of the operations. Further, a computer system, in an embodiment of the present disclosure, is a single device and, in another embodiment, is a distributed computer system comprising multiple devices that operate differently such that the distributed computer system performs the operations described herein and such that a single device does not perform all operations.

The use of any and all examples or exemplary language (e.g., "such as") provided herein is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references including publications, patent applications, and patents cited herein are hereby incorporated by reference to the same extent as if each reference were individually and specifically indicated to be incorporated by reference and were set forth in its entirety herein.

What is claimed is:

1. A modular shelter pod comprising:
    a first panel forming a top or bottom of the modular shelter pod, wherein the first panel includes at least four cavities at first locations each having a first shape and a first cross section;
    a second panel forming the other of the top or the bottom of the modular shelter pod, wherein the second panel includes at least four tabs at second locations corresponding to the first locations, with each of the at least four tabs having a second shape and a second cross section adapted to fit and engage at least four cavities of an adjacent second modular shelter pod to resist movement between the modular shelter pod and the second modular shelter pod when arranged vertically; and
    a third panel removably connecting the first panel and the second panel and forming an opening defining a cleaning port that is sealable by a latch mechanism, the cleaning port shaped to removably engage a cleaning device.

2. The modular shelter pod of claim 1, wherein the cleaning device comprises a UV-C light bulb.

3. The modular shelter pod of claim 1, wherein the cleaning device comprises a conduit, and wherein the modular shelter pod further comprises a drain formed at least in part by the first panel or the second panel.

4. The modular shelter pod of claim 1, further comprising a fourth panel and a fifth panel that are removably connected to at least one of the first panel, the second panel, or the third panel.

5. The modular shelter pod of claim 1, wherein the latch mechanism is removable.

6. The modular shelter pod of claim 4, wherein the first panel, the second panel, the fourth panel, and the fifth panel at least in part form an access opening to an interior of the modular shelter pod.

7. The modular shelter pod of claim 1, wherein the third panel is rotatably connected to the first panel and the second panel, and wherein the modular shelter pod further comprises a fourth panel and a fifth panel that are rotatably connected to at least one of the first panel, the second panel, or the third panel.

8. The modular shelter pod of claim 7, wherein the first panel, the second panel, the third panel, the fourth panel, and the fifth panel rotatably move into a substantially rectangular profile.

9. The modular shelter pod of claim 1, wherein at least one of the first panel, the second panel, or the third panel forms two mechanical receiving devices for accepting an attachment mechanism, wherein the attachment mechanism, when engaged to one of the two mechanical receiving devices, secures the modular shelter pod to the second modular shelter pod in a vertical or horizontal arrangement.

10. The modular shelter pod of claim 1, wherein at least one of the first panel, the second panel, or the third panel forms an attachment mechanism to secure at least one object within an interior of the modular shelter pod formed by the first panel, the second panel, and the third panel.

11. A modular shelter system comprising:
    a plurality of shelter pods stackable on top of each other, wherein individual pods of the plurality of pods further comprise:
    a first panel forming a top or bottom of the pod, wherein the first panel includes at least two cavities at first locations having a first shape and a first cross section;
    a second panel forming the other of the top or the bottom of the pod, wherein the second panel includes at least two tabs at second locations corresponding to the first locations, and having a second shape and a second cross section adapted to fit an engage at least two cavities of the first panel of a second pod of the plurality of pods to resist movement between the first and second pods when the first and second pods are arranged vertically; and
    a third panel connecting the first panel and the second panel and forming an opening defining a cleaning port that is sealable by a latch mechanism, the the cleaning port shaped to removably engage a cleaning device.

12. The system of claim 11, wherein the cleaning device comprises a UV-C light bulb.

13. The system of claim 11, wherein one of the first panel or the second panel comprises a drain that directs fluid from inside an individual pod to outside the individual pod.

14. The system of claim 11, wherein the third panel is removably connected to the first panel and the second panel, and wherein individual pods of the plurality of pods further comprise a fourth panel and a fifth panel that are removably connected to a at least one of the first panel, the second panel, or the third panel.

15. The system of claim 11, wherein the third panel is rotatably connected to the first panel and the second panel, and wherein individual pods of the plurality of pods further comprise a fourth panel and a fifth panel that are rotatably connected to at least one of the first panel, the second panel, or the third panel.

16. The system of claim 15, wherein the first panel, the second panel, the third panel, the fourth panel, and the fifth panel form a substantially rectangular cross section when folded into a transport arrangement.

17. The system of claim 11, wherein at least one of the first panel, the second panel, or the third panel forms a receiver for accepting a attachment mechanism, wherein the modular shelter system further comprises at least one attachment mechanism connecting the first pod to the second pod or to a third pod of the plurality of pods that is adjacent to the first pod.

18. The system of claim 11, further comprising at least three pods stacked vertically.

19. The system of claim 11, further comprising a ladder removably connected to at least one of the first pod or the second pod.

20. The system of claim 11, wherein at least one of the first panel, the second panel, or the third panel are interchangeable for an individual pod or across different pods of the plurality of pods.

* * * * *